United States Patent [19]

Masuda et al.

[11] Patent Number: 4,937,393
[45] Date of Patent: Jun. 26, 1990

[54] METHOD FOR PREPARING ETHYLENE GLYCOL AND/OR PROPYLENE GLYCOL

[75] Inventors: Takayoshi Masuda; Katuyoshi Asano, both of Tokai; Naomi Hori, Chita; Shinji Ando, Nagoya, all of Japan

[73] Assignee: Mitsui Toatsu Chemicals, Incorporated, Tokyo, Japan

[21] Appl. No.: 196,794

[22] Filed: May 17, 1988

Related U.S. Application Data

[63] Continuation of Ser. No. 928,379, Nov. 15, 1986, abandoned.

[30] Foreign Application Priority Data

| Nov. 18, 1985 | [JP] | Japan | 60-256781 |
| Nov. 25, 1985 | [JP] | Japan | 60-262581 |
| Nov. 28, 1985 | [JP] | Japan | 60-266249 |

[51] Int. Cl.$^5$ .................. C07C 29/00; C07C 31/20
[52] U.S. Cl. ............................. 568/867; 568/680
[58] Field of Search ............................. 568/867

[56] References Cited

U.S. PATENT DOCUMENTS

| 2,108,936 | 2/1938 | Ferrero et al. | 568/867 |
| 2,472,417 | 6/1949 | Gouze | 568/867 |
| 2,784,202 | 3/1957 | Gardner et al. | 568/867 |
| 3,062,889 | 11/1962 | Murphy | 568/867 |
| 3,071,601 | 1/1963 | Aries | 568/867 |
| 3,576,890 | 4/1971 | Binning | 568/867 |
| 4,112,054 | 9/1978 | Feingold | 568/867 |
| 4,277,632 | 7/1981 | Kumazawa et al. | 568/867 |
| 4,339,616 | 7/1982 | Rutzen et al. | 568/867 |
| 4,358,625 | 11/1982 | Piggimi et al. | 568/867 |
| 4,626,603 | 12/1986 | Siegmeier et al. | 568/867 |

FOREIGN PATENT DOCUMENTS

| 2141470 | 2/1973 | Fed. Rep. of Germany | 568/867 |
| 2256907 | 5/1974 | Fed. Rep. of Germany | 568/867 |

OTHER PUBLICATIONS

S. A. Miller, "Ethylene and its Industrial Derivatives", pp. 588–594, (Ernest Benn Ltd., 1969).

*Primary Examiner*—J. E. Evans
*Attorney, Agent, or Firm*—Oblon, Spivak, McClelland, Maier & Neustadt

[57] ABSTRACT

In the manufacturing method of ethylene glycol and/or propylene glycol, these glycols can be prepared with a highly selectivity and at a high yield by applying the catalyst comprising a carboxylic acid and a carboxylic acid salt or a metal salt of formic acid alone.

10 Claims, No Drawings

METHOD FOR PREPARING ETHYLENE GLYCOL AND/OR PROPYLENE GLYCOL

This application is a continuation of application Ser. No. 06/928,379, filed on Nov. 10, 1986, now abandoned.

BACKGROUND OF THE INVENTION

(1) Field of the Invention

This invention relates to a method for preparing ethylene glycol and/or propylene glycol. More particularly, it relates to a method for preparing ethylene glycol and/or propylene glycol with a catalyst comprising a carboxylic acid and a carboxylic acid salt or a metal salt of formic acid alone.

(2) Description of the Prior Art

Conventionally, as methods for preparing lower alkylene glycols, there is widely employed in industry methods for conducting a hydration reaction of lower alkylene oxides as epoxy compounds with water without catalysts or with acid catalysts, for example, mineral acids such as sulfuric acid [for example, refer to S. A. Miller, Ethylene and its Industrial Derivatives, page 588–594 (Ernest Benn Ltd., 1969)].

This process, however, requires to depress as much as possible the formation of by-products including diethylene glycol, triethylene glycol, dipropylene glycol and tripropylene glycol which are commercially in a small demand. Thus it is forced to employ a large excess of water, the quantity of which is about 10 to about 30 miles per 1 mole of the lower alkylene oxide, and the desired lower alkylene glycols were obtained only as dilute aqueous solutions.

Therefore, the process has a disadvantage that, after the end of hydration reaction, a large amount of energy is consumed in order to concentrate, dehydrate and fractionate the reaction mixture and thus it becomes economically unfavorable unfavorable.

Base catalysts have the effect of accelerating the hydration reaction, however, they generally increase the quantity of by-products as compared with the above described reactions without catalysts or with acid catalysts. Since the selectivity of desired lower alkylene glycols is apt to decrease (for example, refer to above Ethylene and its Industrial Derivatives, page 594, lines 16–24), the hydration reaction with the base catalysts has not been applied in industry.

On the other hand, a method has recently been proposed to overcome the drawbacks of the above described manufacturing process, wherein lower alkylene oxides are hydrated in high concentrations with equivalent amounts of water in the presence of carbon dioxide and with tetraalkyl ammonium salts or quarternary phosphonium salts as a catalyst.

The above described method of conducting the hydration reaction in the presence of carbon dioxide has not yet satisfactorily developed in view of the catalyst and cost performance. It has also a disadvantage that the method uses a large amount of carbon dioxide (generally employed in the form of gas), thus requires relatively high reaction pressure as compared with the above described methods of industrial production which are currently in a wide application, and leads to a high construction cost of the plant.

Therefore, development of a novel hydration reaction technology is now earnestly desired which enables the hydration reaction of lower alkylene oxides in high concentrations and also can prepare lower alkylene glycols more favorably with a high selectivity and at a high yield.

SUMMARY OF THE INVENTION

The object of this invention is to provide a catalyst having a high selectivity and a high yield in a method of preparing ethylene glycol and/or propylene glycol.

The object of this invention can be achieved by applying a carboxylic acid and a carboxylic acid salt in combination or a metal salt of formic acid alone.

DETAILED DESCRIPTION OF THE INVENTION

The raw material for use in the method of this invention for the preparation of ethylene glycol and/or propylene glycol is a lower alkylene oxide which includes, for example, ethylene oxide and/or propylene oxide. Every oxide is generally employed for the hydration reaction independently to the preparation of ethylene glycol or propylene glycol and both oxides may also be used in combination.

Water as the other raw material is not restricted in particular. Any water can be used which includes city water, ion exchange water, steam condensate and condensed water recovered from condensation and dehydration processes of water containing crude lower alkylene glycol in the manufacturing equipment of the lower alkylene glycol which is for use in the method of this invention.

The quantity of water may be reduced to the stoichiometric amount. It may be further decreased according to the type of reaction, but at least the stoichiometric amount of water is desired from a practical point of view.

Actually, 1–15 moles of water, preferably 1–7 moles and most preferably 1–15 per 1 mole of the lower alkylene oxide.

Water may be employed more than 15 moles, however, as described above, the use of a large amount of water is unfavorable on energy consumption and the above range of water is practically sufficient.

It is most advantageous to use water in the smallest required quantity of about 1 to about 3 moles per 1 mole of the lower alkylene oxide from a general view point. The general view point means the industrially allowable limit of by-products such as dialkylene glycol, tiralkylene glycol etc. and reduction of energy consumption in the total manufacturing steps including concentration, dehydration and fractional distillation after the hydration reaction.

According to the results of the inventors' examination, when the carboxylic acid is employed singly as the catalyst for the hydration reaction of lower alkylene oxide, the effect of accelerating the hydration rate is recognized, but almost no effect is found for inhibiting the formation of the by-products including dialkyleneglycol, trialkyleneglycol etc. In addition, when the metal salt of carboxylic acid is used singly as the catalyst, the effect of accelerating the hydration reaction is recognized, but only the metal salt of carboxylic acid having small carbon numbers has the effect of inhibiting the formation of the by-products. Furthermore, the effect of catalysts other than the metal salt of formic acid is unsatisfactory.

When the metal salt of formic acid or a dual catalyst composed of a carboxylic acid and a metal salt of carboxylic acid is used, a remarkably inhibiting effect for the formation of by-products is exhibited and the effect of dual catalyst becomes unlimited to a particular carboxylic acid.

As described above, metal salts of aliphatic lower mono-carboxylic acids such as acetic acid and propionic acid has also catalytic effect to some extent, however, the effect is much inferior to that of the metal salt of formic acid and can not be applied at all for practical use. Almost no catalytic effect is exhibited by metal salts of aromatic carboxylic acids such as benzoic acid and those of aliphatic divalent carboxylic acids such as oxalic acid, malonic acid and succinic acid. Therefore, the excellent effect of the metal salt of formic acid is regarded as a specific property.

The metal salt of formic acid for use in the method of this invention includes, as typical examples, alkali metal salt such as lithium, sodium and potassium salts, alkali earth metal salt such as magnesium, calcium and barium salts, and metal salt of copper, zinc, aluminum, titanium, manganese and iron groups. Most preferred are alkali and alkali earth metals of formic acid in particular.

The above described metal salt of formic acid is not always required to prepare in advance. Explaining the case of alkali metal salt as an example, it is also possible to use a method wherein free formic acid and alkali metal and/or at least one of the alkali metal compounds selected from the group consisting of alkali metal hydroxide, alkali metal carbonate, alkali metal hydrogen carbonate and alkali metal oxide are separately charged into a hydration reaction vessel in order to form the salt of both materials, that is, the alkali metal salt of formic acid in said reaction vessel. Such a method, of course, is also included in the scope of this invention. The amount of catalyst for use cannot uniformly be defined, since it depends upon the type of metal salt. The amount may be 1-50 moles, preferably 2-30 moles and most preferably 3-20 moles per 100 moles of the lower alkylene oxide.

The effect cannot be fully exhibited when the quantity of the catalyst is less than the above described lower limit. When the catalyst is used in a large quantity exceeding the upper limit, it is not economical and thus the above described range is suitable for practice.

The carboxylic acid which is one component in the dual catalyst composition for use in this invention is a generic term of a compound having at least one carboxyl group (—COOH) in the molecule. More concretely, it includes aliphatic carboxylic acid having a short or long chain (so-called fatty acid), cycloaliphatic carboxylic acid, aralkyl carboxylic acid and aromatic carboxylic acid.

The carboxylic acid having about 1 to about 20 carbon atoms is generally used. Monobasic or polybasic carboxylic acid having more preferably 1-10 carbon atoms, and most preferably 1-7 carbon atoms is employed due to the catalyst performance per unit mole as well as per unit weight. Unless affecting negative effect on the catalyst performance by thermal degradation or side reaction caused by the existing functional groups in the hydrating conditions of this invention, said carboxylic acid may have substituents which include alkyl, halogeno, nitro, cyano and methoxy groups.

A typical example of the carboxylic acid is aliphatic carboxylic acid which includes formic acid, acetic acid, propionic acid, n-butyric acid, i-butyric acid, n-varelic acid, i-valeric acid, trimethyl acetic acid, caproic acid, caprylic acid, capric acid, 2-butyl-5-methylpentanoic acid, 2,3-dimethyloctanoic acid, lauric acid, myristic acid, palmitic acid, stearic acid, oxalic acid, malonic acid, succinic acid, gultaric acid, adipic acid, pimelic acid, suberic acid, azelaic acid, sebacic acid, fluoroacetic acid, chloroacetic acid, dichloroacetic acid, trichloroacetic acid, glycolic acid, lactic acid, malic acid, tartaric acid, citric acid, thioglycollic acid, methoxyacetic acid, cyanoacetic acid, acrylic acid, methacrylic acid, cortonic acid, i-crotonic acid, 2-hexenoic acid, 4-hexenoic acid, caproleic acid, oleic acid, maleic acid and fumaric acid; cycloaliphatic carboxylic acid which includes cyclopentanecarboxylic acid and cyclohexanecarboxylic acid; aralkyl carboxylic acid which includes phenylacetic acid, diphenylacetic acid and benzylmalonic acid; and aromatic carboxylic acid which includes benzoic acid, o-toluic acid, m-toluic acid, p-toluic acid, p-chlorobenzoic acid, o-nitrobenzoic acid, p-methoxybenzoic acid, $\beta$-naphthoic acid, phthalic acid, isophthalic acid, terephthalic acid, trimellitic acid and pyromellitic acid.

The carboxylic acid salt which is the other component in the dual catalyst composition of this invention is a metal salt or a salt of basic-nitrogen containing compound. A typical example of the metal salt is the salt of the above described carboxylic acid which includes alkali metal salt such as lithium salt, sodium salt and potassium salt; alkali earth metal salt such as magnesium salt, calcium salt and barium salt; copper group metal salt, zinc group metal salt, aluminium group metal salt, titanium group metal salt, manganese group metal salt and iron group metal salt. Particularly the salt of alkali and alkali earth metals is used most preferably.

The above described various carboxylic acid and carboxylic acid salt can be used in an arbitrary combination of not less than one compound from each concretely illustrated group.

Besides, the metal salt of the carboxylic acid is not always required to prepare in advance. Explaining the case of the alkali metal salt as an example, it is also possible to use a method wherein at least one of the carboxylic acid and alkali metal and/or not less than one of the alkali metal compound selected from the group consisting of alkali metal hydroxide, alkali metal carbonate, alkali metal hydrogen carbonate and alkali metal oxide are separately charged into a hydration reaction vessel in order to form the salt of both materials, that is, the alkali metal salt of the carboxylic acid in said reaction vessel.

The employed ratio of the carboxylic acid to the metal salt of the carboxylic acid is 100:1-1:100 by mole, preferably 100:3-3:100 by mole, and most preferably 100:5-5:100 by mole. When the ratio of these two materials is outside the above range, it is unfavorable because the effect of this invention cannot be fully exhibited.

In addition, the employed total quantity of the carboxylic acid and the metal salt of the carboxylic acid is 0.1-50 moles, preferably 0.5-30 moles, and most preferably 1-20 moles per 100 moles of the lower alkylen oxide.

The effect cannot be fully exhibited when the total quantity of both materials for use is less than the above described lower limit. When the total quantity is in excess of the upper limit, it is not economical and thus the above described range is suitable for practice.

The salt of the basic-nitrogen containing compound which is another group of the carboxylic acid salt component in the dual catalyst composition is the salt of the above described carboxylic acid with the basic-nitrogen containing compound.

A typical example of the basic-nitrogen containing compound which is a component of said salt includes, for example, an inorganic nitrogen containing compound represented by ammonia, hydrazine and hydroxylamine; aliphatic primary, secondary or tertiary amine such as methylamine, dimethylamine, trimethylamine, ethylamine, diethylamine, triethylamine, N,N-diethylmethylamine, tripropylamine, tri-i-propylamine, tributylamine, actylamine, dioctylamine, trioctylamine, triallylamine, N,N-dimethylallylamine, ethanolamine, diethanolamine, triethanolamine, tri-i-propanolamine, 3-methoxypropylamine, N,N-dimethylethanolamine, N,N-diethylethanolamine, N-methylethanolamine, ethylene diamine, N,N,N'-trimethylethylenediamine, N,N,N',N'-tetramethylethylenediamine, N,N,N',N'-tetraethylethylenediamine, 1,2-propanediamine, 1,3-propanediamine, hexamethylenediamine, N,N,N',N'-tetramethylhexamethylenediamine and diethylenetriamine; an aliphatic nitrogen containing compound having a particular structure such as guanidine and amidine; cycloaliphatic primary, secondary or tertiary amine such as cyclohexylamine, N-methylcyclohexylamine and N,N-dimethylcyclohexylamine; aralkyl primary, secondary or tertiary amine such as benzylamine, N-methylbenzylamine and N,N-dimethylbenzylamine; aromatic primary, secondary or tertiary amine such as aniline, N-methylaniline, N,N-dimethylaniline, diphenylamine, triphenylamine, o-toluidine, m-toluidine, p-toluidine, o-anisidine, p-chloroaniline, o-nitroaniline, o-phenylenediamine, m-phenylenediamine, p-phenylenediamine, β-naphthylamine and N,N-dimethyl-β-naphthylamine; and a nitrogen containing heterocyclic compound such as ethyleneimine, N-methylethyleneimine, N-phenylethyleneimine, azetidine, pyrrolidine, N-ethylpyrrolidine, piperidine, piperazine, N,N-dimethylpiperazine, morpholine, N-ethylmorpholine pyrrole, pyridine, α-picoline, β-picoline, γ-picoline, 2,6-lutidine, 3-cyanopyridine, nicotinic amide, 2-chloropyridine, indole, quinoline, isoquinoline, imidazole, pyrazole, oxazole, thiazole, pyrazine, pyrimidine, triazine and 1,5-diazabicyclo(4,3,0)nonene5 having a cyclic amidine structure.

The above described various carboxylic acid and the carboxylic acid salt of the basic-nitrogen containing compound can be used in an arbitrary combination of not less than one compound from each concretely illustrated group.

The carboxylic acid salt of the basic-nitrogen containing compound is not always required to prepare in advance. It is also possible to use a method wherein at least each one of the above described carboxylic acid and the basic-nitrogen containing compound is separately charged into a hydration reaction vessel in order to form the salt of both materials in said vessel.

The ratio for use of the carboxylic acid to the carboxylic acid salt of the basic-nitrogen containing compound is 100:1–1:100 by mole, preferably 100:3–3:100 by mole and most preferably 100:5–5:100 by mole. When the ratio of these two materials is outside the above described range, it is unfavorable because the effect of this invention cannot be fully exhibited.

The employed total quantity of the carboxylic acid and the carboxylic acid salt of the basic-nitrogen containing compound is 0.1–50 moles, preferably 0.5–30 moles and most preferably 1–20 moles per 100 moles of the lower alkylene oxide. The effect cannot be fully exhibited when the total quantity of both materials for use is less than the above described lower limit. It is not economical when the total quantity is in excess of the upper limit. Thus any of these cases are unfavorable.

The hydration reaction is generally conducted in the liquid phase. Any type of batchwise, semi-batchwise or continuous reaction is suitable for this purpose. A type of the reaction vessel is not limited, so far as it is designed to sufficiently contact the lower alkylene oxide, water and the catalyst with each other and to remove reaction heat. For example, an agitator-equipped drump type reactor or a tubular reactor can arbitrarily be used.

The reaction temperature depends upon the kind and quantity of the catalyst, the kind of lower alkylene oxide and the mole ratio of lower alkylene oxide to water. It may not uniformly be defined and is at a range of 30°–300° C, preferably 50°–250° C. and most preferably 80°–200° C.

The reaction time which also depends on the same factors, is at the range of 1 minute to 10 hours, preferably 10 minutes to 5 hours and most preferably 30 minutes to 3 hours.

The reaction pressure is preferably maintained at the level of keeping the lower alkylene oxide in the liquid state. It is generally 0–50 kg/cm$^2$G, preferably 3–40 kg/cm$^2$G and most preferably 5–30 kg/cm$^2$G.

The carboxylic acid salt is generally used after dissolving into water or a mixture of water with ethylene glycol and/or propylene glycol, and can also be used in the form of slurry.

The carboxylic acid is generally used after dissolving into a liquid including water and a mixture of water with ethylene glycol and/or propylene glycol, and can also be fed into a reactor as it is.

After the hydration reaction, the residual water and the catalyst in the reaction mixture are removed by an arbitrary process including, for example, distillation, evaporation and crystallization. Desired lower alkylene glycol can be purified by distillation to afford a high purity product.

It is economical to recover and reuse the catalyst.

Since the method of this invention leads to a remarkable reduction in the quantity of water for use in the hydration reaction and enables to proceed the reaction in a high concentration, the reaction mixture after the hydration reaction can be obtained as an aqueous solution of the lower alkylene glycol having a high concentration. Furthermore, the desired lower alkylene glycol can be prepared with a high selectivity and at a high yield.

Since the reaction rate of hydration increases as compared with a noncatalytic reaction, equipment efficiency and productivity can be remarkably improved with the realization of hydration reaction in the high concentration.

Furthermore, it is a great advantage that the hydration reaction can proceed in the absence of carbon dioxide.

Therefore, the method of this invention is very advantageous in reducing energy and resources consumption, and is highly profitable in the industry.

DESCRIPTION OF THE PREFERRED EMBODIMENT

The invention will be further illustrated with respect to the following Examples and Comparative Examples. These examples are merely illustrative of the present invention without being deemed limitative in any manner thereof.

EXAMPLE 1

In a stainless steel autoclave having a capacity of 200 ml and equipped with a stirrer, a thermometer and a pressure gauge were charged 58 grams (1 mole) of propylene oxide, 36 grams (2 moles) of water and 2.04 grams (0.03 moles) of sodium formate. Said autoclave was set in an electric furnace and heated under stirring to an internal temperature of 160° C. and conducted the reaction for an hour at this temperature.

The internal pressure of the reaction vessel was rised to a maximum of 15 kg/cm$^2$G and then reduced with the progress of hydration reaction to a final pressure of 5 kg/cm$^2$G at the end of reaction.

The autoclave was then cooled to the room temperature. A part of the reaction mixture was collected and a quantitative analysis was carried out by gas chromatography on the unreacted propylen oxide and the product of propylene glycol, dipropylene glycol and tripropylene glycol. The results are illustrated in Table 1.

EXAMPLES 2-9

The same autoclave in Example 1 was used. Reaction conditions such as quantity of raw materials, kind and quantity of the catalyst and reaction temperature were varied as illustrated in Table 1 to perform the hydration reaction of propylene oxide. The results are illustrated in Table 1.

COMPARATIVE EXAMPLE 1

The procedure similar to that of Example 1 was repeated without any catalyst to carry out the hydration reaction of propylene oxide. The results are illustrated in Table 1.

COMPARATIVE EXAMPLE 2

The procedure similar to that of Example 1 was repeated to carry out the hydration reaction of propylene oxide except 2.46 grams (0.03 mole) of sodium acetate were employed in place of sodium formate. The results are illustrated in Table 1.

COMPARATIVE EXAMPLE 3

The procedure similar to that of Example 1 was repeated to perform the hydration reaction of propylene oxide except 4.32 grams (0.03 mole) of sodium benzoate were used in place of sodium formate. The results are illustrated in Table 1.

COMPARATIVE EXAMPLE 4

The procedure similar to that of Example 1 was repeated to conduct the hydration reaction of propylene oxide except 4.02 grams (0.03 mole) of disodium oxalate were applied in place of sodium formate. The results are illustrated in Table 1.

TABLE 1

| Example No. | Material PO (g) | H$_2$O (g) | H$_2$O/PO [mole ratio] | Catalyst (A) Salt | Quantity (g) | (A)/PO (% mole) | Reaction Temperature (°C.) | Time (hr) | Conversion (% mole) | PG (% wt) | Product DPG (% wt) | TPG (% wt) |
|---|---|---|---|---|---|---|---|---|---|---|---|---|
| 1 | 58 | 36 | 2 | For Na | 2.04 | 3 | 160 | 1 | 100 | 78.4 | 19.8 | 1.8 |
| 2 | 58 | 36 | 2 | For Na | 3.4 | 5 | 160 | 1 | 100 | 85.4 | 13.3 | 1.3 |
| 3 | 58 | 36 | 2 | For Na | 6.8 | 10 | 160 | 1 | 100 | 90.8 | 8.7 | 0.5 |
| 4 | 58 | 18 | 1 | For Na | 3.4 | 5 | 160 | 1 | 99.7 | 86.3 | 12.7 | 1.0 |
| 5 | 58 | 18 | 1 | For K | 4.2 | 5 | 160 | 1 | 99.9 | 87.0 | 12.1 | 0.9 |
| 6 | 58 | 36 | 2 | For K | 6.72 | 8 | 160 | 1 | 100 | 90.2 | 9.0 | 0.8 |
| 7 | 58 | 36 | 2 | For Li | 2.6 | 5 | 160 | 1 | 99.9 | 84.9 | 13.7 | 1.4 |
| 8 | 58 | 36 | 2 | For Ca | 6.5 | 5 | 160 | 2 | 100 | 87.5 | 11.6 | 0.9 |
| 9 | 58 | 36 | 2 | For Na | 3.4 | 5 | 120 | 1 | 99.8 | 85.6 | 13.2 | 1.2 |
| Compar 1 | 58 | 36 | 2 | — | — | — | 160 | 1 | 96.5 | 59.3 | 30.4 | 10.3 |
| Compar 2 | 58 | 36 | 2 | Ac Na | 2.46 | 3 | 160 | 1 | 100 | 68.4 | 27.5 | 4.1 |
| Compar 3 | 58 | 36 | 2 | Ben Na | 4.32 | 3 | 160 | 1 | 100 | 61.9 | 30.0 | 8.1 |
| Compar 4 | 58 | 36 | 2 | Oxa Na | 4.02 | 3 | 160 | 1 | 100 | 61.5 | 30.1 | 8.4 |

Note:
PO ... propylene oxide
H$_2$O ... water
PG ... propylene glycol
DPG ... dipropylene glycol
TPG ... tripropylene glycol
For Na ... sodium formate
For K ... potassium formate
For Li ... lithium formate
For Ca ... calcium formate
Ac Na ... sodium acetate
Ben Na ... sodium benzoate
Oxa Na ... disodium oxalate

EXAMPLE 10

In the same autoclave in Example 1 were charged 44 grams (1 mole) of ethylene oxide, 36 grams (2 moles) of water and 6.8 grams (0.1 mole) of sodium formate. The autoclave was heated to 140° C. under stirring and the reaction was carried out for an hour at this temperature.

The procedure similar to that of Example 1 was repeated for the analysis of the reaction mixture. The conversion ratio of ethylene oxide was 100%. Besides the reaction product was composed of 91.5% of ethylene glycol by weight, 7.8% of diethylene glycol by weight and 0.7% of triethylene glycol by weight.

EXAMPLE 11

In the same autoclave in Example 1 were charged 58 grams (1 mole) of propylene oxide, 36 grams (2 moles) of water, 1.2 grams (0.02 mole) of acetic acid and 2.46 grams (0.03 mole) of sodium acetate.

Said autoclave was set in an electric furnace and heated under stirring to an internal temperature of 160° C. and carried out the reaction for one hour at this temperature. Then the internal pressure was reduced with the progress of hydration reaction to a final pressure of 4.5 kg/cm$^2$G at the end of reaction.

The autoclave was then cooled to the room temperature, a part of the reaction mixture was collected and the same quantitative analyses as in Example was conducted. The results are illustrated in Table 2.

EXAMPLES 12-31

The same autoclave in Example 1 was used. Reaction conditions such as quantity of raw materials, kind and quantity of the catalyst and reaction temperature were varied as illustrated in Table 2 to perform the hydration reaction of propylene oxide. The results are illustrated in Table 2.

COMPARATIVE EXAMPLE 5

The procedure similar to that of Example 11 was repeated without any catalyst to carry out the hydration reaction of propylene oxide. The results are illustrated in Table 2.

COMPARATIVE EXAMPLE 6

The procedure similar to that of Example 11 was repeated to carry out the hydration reaction of propylene oxide except that 2.46 grams (0.03 mole) of sodium acetate were used without acetic acid. The results are illustrated in Table 2.

COMPARATIVE EXAMPLE 7

The procedure similar to that of Example 11 was repeated to carry out the hydration reaction of propylene oxide except that 1.2 grams (0.02 mole) of acetic acid were used without sodium acetate. The results are illustrated in Table 2.

COMPARATIVE EXAMPLE 8

The procedure similar to that of Example 18 was repeated to carry out the hydration reaction of propylene oxide except that 2.04 grams (0.03 mole) of sodium formate were used without formic acid. The results are illustrated in Table 2.

COMPARATIVE EXAMPLE 9

The procedure similar to that of Example 18 was repeated to carry out the hydration reaction of propylene oxide except that 0.69 gram (0.015 mole) of formic acid was used without sodium formate. The results are illustrated in Table 2.

COMPARATIVE EXAMPLE 10

The procedure similar to that of Example 26 was repeated to carry out the hydration reaction of propylene oxide except that 4.32 grams (0.03 mole) of sodium benzoate were used without formic acid. The results are illustrated in Table 2.

TABLE 2

| Example No. | Material | | | Catalyst | | | | Reaction Temperature (°C.) | Time (hr) | Conversion (% mole) | Product | | |
|---|---|---|---|---|---|---|---|---|---|---|---|---|---|
| | PO (g) | $H_2O$ (g) | $H_2O/PO$ [mole ratio] | (A) Acid (g) [mole] | (B) Salt (g) [mole] | (A)/(B) [mole ratio] | (A)+(B)/PO [% mole] | | | | PG (% wt) | DPG (% wt) | TPG (% wt) |
| 11 | 58 | 36 | 2 | Acetic 1.2 [0.02] | Ac Na 2.46 [0.03] | 66.7/100 | 5 | 160 | 1 | 100 | 85.5 | 12.8 | 1.7 |
| 12 | 58 | 36 | 2 | Acetic 0.6 [0.01] | Ac Na 4.1 [0.05] | 20/100 | 6 | 160 | 1 | 100 | 92.1 | 7.2 | 0.7 |
| 13 | 58 | 36 | 2 | Acetic 3.0 [0.05] | Ac Na 2.46 [0.03] | 100/60 | 8 | 160 | 1 | 100 | 93.2 | 6.3 | 0.5 |
| 14 | 56 | 36 | 2 | Acetic 6.0 [0.1] | Ac Na 1.64 [0.02] | 100/20 | 12 | 160 | 1 | 100 | 91.7 | 7.5 | 0.8 |
| 15 | 58 | 18 | 1 | Acetic 0.6 [0.01] | Ac K 2.94 [0.03] | 33.3/100 | 4 | 160 | 1 | 100 | 92.7 | 6.8 | 0.5 |
| 16 | 58 | 18 | 1 | Acetic 0.6 [0.01] | Ac Ca 4.74 [0.03] | 33.3/100 | 4 | 160 | 1 | 100 | 91.5 | 7.9 | 0.6 |
| 17 | 58 | 18 | 1 | Acetic 1.8 [0.03] | Ac Mg 4.26 [0.03] | 100/100 | 6 | 160 | 1 | 100 | 92.2 | 7.3 | 0.5 |
| 18 | 58 | 18 | 1 | Formic 0.69 [0.015] | For Na 2.04 [0.03] | 50/100 | 4.5 | 140 | 1 | 100 | 96.1 | 3.8 | 0.1 |
| 19 | 58 | 18 | 1 | Formic 0.092 [0.002] | For Na 3.4 [0.05] | 4/100 | 5.2 | 140 | 1 | 100 | 95.3 | 4.6 | 0.1 |
| 20 | 58 | 18 | 1 | Formic 4.6 [0.1] | For Na 1.36 [0.02] | 100/20 | 12 | 140 | 1 | 100 | 93.1 | 6.5 | 0.4 |
| 21 | 58 | 18 | 1 | Formic 4.6 [0.1] | For Na 0.68 [0.01] | 100/10 | 11 | 140 | 1 | 100 | 92.5 | 7.0 | 0.5 |
| 22 | 58 | 18 | 1 | Formic 0.276 [0.006] | For K 2.52 [0.03] | 20/100 | 3.6 | 140 | 1 | 100 | 95.1 | 4.8 | 0.1 |
| 23 | 58 | 18 | 1 | Formic 1.38 [0.03] | For Ca 3.9 [0.03] | 100/100 | 6 | 140 | 1 | 100 | 93.8 | 5.9 | 0.3 |
| 24 | 58 | 18 | 1 | Formic 1.38 [0.03] | Pro Na 2.88 [0.03] | 100/100 | 6 | 140 | 1 | 100 | 94.7 | 5.1 | 0.2 |

TABLE 2-continued

| Example No. | Material PO (g) | Material H₂O (g) | Material H₂O/PO [mole ratio] | Catalyst (A) Acid (g) [mole] | Catalyst (B) Salt (g) [mole] | Catalyst (A)/(B) [mole ratio] | (A)+(B)/PO [% mole] | Reaction Temperature (°C.) | Time (hr) | Conversion (% mole) | Product PG (% wt) | Product DPG (% wt) | Product TPG (% wt) |
|---|---|---|---|---|---|---|---|---|---|---|---|---|---|
| 25 | 58 | 18 | 1 | Formic 0.69 [0.015] | Oxa Na 4.02 [0.03] | 50/100 | 4.5 | 140 | 1 | 100 | 93.5 | 6.1 | 0.4 |
| 26 | 58 | 18 | 1 | Formic 1.38 [0.03] | Ben Na 4.32 [0.03] | 100/100 | 6 | 140 | 1 | 100 | 92.1 | 7.2 | 0.7 |
| 27 | 58 | 18 | 1 | Formic 1.38 [0.03] | Lau Na 11.8 [0.05] | 60/100 | 8 | 140 | 1 | 100 | 91.8 | 7.4 | 0.8 |
| 28 | 58 | 18 | 1 | Propionic 0.74 [0.01] | For Na 2.04 [0.03] | 33.3/100 | 4 | 160 | 1 | 100 | 92.0 | 7.2 | 0.8 |
| 29 | 58 | 18 | 1 | Cl-Acetic 0.945 [0.01] | ClAcNa 2.33 [0.02] | 50/100 | 3 | 140 | 1 | 100 | 94.0 | 5.6 | 0.4 |
| 30 | 58 | 18 | 1 | Oxalic 0.9 [0.01] | Oxa Na 2.68 [0.02] | 50/100 | 3 | 140 | 1 | 100 | 94.2 | 5.5 | 0.3 |
| 31 | 58 | 18 | 1 | Benzoic 3.66 [0.03] | Ben Na 4.32 [0.03] | 100/100 | 6 | 160 | 1 | 100 | 90.8 | 8.0 | 1.2 |
| Compar 5 | 58 | 36 | 2 | — | — | — | — | 160 | 1 | 96.5 | 59.3 | 30.4 | 10.3 |
| Compar 6 | 58 | 36 | 2 | — | Ac Na 2.04 [0.03] | 0/100 | 3 | 160 | 1 | 100 | 68.4 | 27.5 | 4.1 |
| Compar 7 | 58 | 36 | 2 | Acetic 1.2 [0.02] | — | 100/0 | 2 | 160 | 1 | 99.7 | 60.0 | 29.5 | 10.5 |
| Compar 8 | 58 | 18 | 1 | — | For Na 2.04 [0.03] | 0/100 | 3 | 140 | 1 | 100 | 77.7 | 20.1 | 2.2 |
| Compar 9 | 58 | 18 | 1 | Formic 0.69 [0.015] | — | 100/0 | 1.5 | 140 | 1 | 100 | 59.9 | 30.1 | 10.0 |
| Compar 10 | 58 | 18 | 1 | — | Ben Na 4.32 [0.03] | 0/100 | 3 | 140 | 1 | 100 | 61.1 | 29.8 | 9.1 |

Note:
PO ... propylene oxide
H₂O ... water
PG ... propylene glycol
DPG ... dipropylene glycol
TPG ... tripropylene glycol
Cl-Acetic ... monochloroacetic acid
Ac Na ... sodium acetate
Ac K ... potassium acetate
Ac Ca ... calcium acetate
Ac Mg ... magnesium acetate
For Na ... sodium formate
For K ... potassium formate
For Ca ... calcium formate
Pro Na ... sodium propionate
Oxa Na ... disodium oxalate
Ben Na ... sodium benzoate
Lau Na ... sodium laurate
ClAcNa ... sodium monochloroacetate

EXAMPLE 32

In the same autoclave in Example 1 were charged 44 grams (1 mole) of ethylene oxide, 27 grams (1.5 moles) of water, 1.2 grams (0.02 mole) of acetic acid and 4.1 grams (0.05 moles) of sodium acetate, and heated to 140° C. under stirring. The reaction was carried out for an hour at this temperature.

The reaction mixture was analyzed by the same procedure as in Example 1. The conversion ratio of ethylene oxide was 100%. The reaction product was composed of 93.6% of ethylene glycol by weight, 6.1% of diethylene glycol by weight and 0.3% of triethylene glycol by weight.

EXAMPLE 33

As in Experiment 32, 44 grams (1 mole) of ethylene oxide, 18 grams (1 mole) of water, 0.92 grams (0.02 mole) of formic acid and 2.72 grams (0.04 mole) of sodium formate were used. The reaction was conducted for one hour at 140° C.

The reaction mixture was analyzed by the same method as in Example 1. The conversion rate of ethylene oxide was 100%. The reaction product was composed of 94.3% of ethylene glycol by weight, 5.5% of diethylene glycol by weight and 0.2% of triethylene glycol by weight.

EXAMPLE 34

In the same autoclave in Example 1 were charged 58 grams (1 mole) of propylene oxide, 36 grams (2 moles) of water, 1.9 grams (0.03 mole) of acetic acid and 3.57 grams (0.03 mole) of trimethylamine acetate. Said autoclave was set in an electric furnace and heated under stirring to an internal temperature of 160° C. and the reaction was conducted for one hour at this temperature.

The internal pressure of the reactor was risen to a maximum of 15 kg/cm$^2$G and then reduced with the progress of hydration reaction to a final pressure of 4.5 kg/cm$^2$G at the end of reaction.

The autoclave was cooled to the room temperature and a part of the reaction mixture was collected and analyzed by the same method as Example 1. The results are illustrated in Table 3.

EXAMPLES 35–45

The same autoclave in Example 1 was used. Reaction conditions such as quantity of raw materials, kind and quantity of the catalyst and reaction temperature were varied as illustrated in Table 3 to perform the hydration reaction of propylene oxide. The results are illustrated in Table 3.

COMPARATIVE EXAMPLE 11

The procedure similar to that of Example 34 was repeated without any catalyst to carry out the hydration reaction of propylene oxide. The results are illustrated in Table 3.

COMPARATIVE EXAMPLE 12

The procedure similar to that of Example 34 was repeated to carry out the hydration reaction of propylene oxide except that 3.57 grams (0.03 mole) of trimethylamine acetate were used without acetic acid. The results are illustrated in Table 3.

COMPARATIVE EXAMPLE 13

The procedure similar to that of Example 34 was repeated to carry out the hydration reaction of propylene oxide except that 1.8 grams (0.03 mole) of acetic acid were used without trimethylamine acetate. The results are illustrated in Table 3.

COMPARATIVE EXAMPLE 14

The procedure similar to that of Example 40 was repeated to carry out the hydration reaction of propylene oxide except that 3.08 grams (0.04 mole) of ammonium acetate were used without acetic acid. The results are illustrated in Table 3.

EXAMPLE 46

In the same autoclave in Example 1 were charged 44 grams (1 mole) of ethylene oxide, 27 grams (1.5 moles) of water, 0.3 grams (0.005 mole) of acetic acid, and 5.95 grams (0.05 mole) of trimethylamine acetate, and heated under stirring to 140° C. The reaction was conducted for an hour at this temperature.

The reaction mixture was analyzed by the same method as in Example 1. The conversion ratio of ethylene oxide was 100%. The reaction product was composed of 93.9% of ethylene glycol by weight, 5.9% of diethylene glycol by weight and 0.2% of triethylene glycol by weight.

TABLE 3

| Example No. | PO (g) | H$_2$O (g) | H$_2$O/PO (mole ratio) | (A) Acid (g) [mole] | (B) Salt (g) [mole] | (A)/(B) [mole ratio] | (A)+(B)/PO [% mole] | Reaction Temperature (°C.) | Time (hr) | Conversion (% mole) | PG (% wt) | DPG (% wt) | TPG (% wt) |
|---|---|---|---|---|---|---|---|---|---|---|---|---|---|
| 34 | 58 | 36 | 2 | Acetic 1.8 [0.03] | Ac TEA 3.57 [0.03] | 100/100 | 6 | 160 | 1 | 100 | 91.5 | 7.6 | 0.9 |
| 35 | 58 | 36 | 2 | Acetic 0.6 [0.01] | Ac TEA 5.95 [0.05] | 20/100 | 6 | 160 | 1 | 100 | 93.1 | 6.4 | 0.5 |
| 36 | 58 | 36 | 2 | Acetic 6.0 [0.1] | Ac TEA 2.38 [0.02] | 100/20 | 12 | 160 | 1 | 100 | 92.7 | 6.8 | 0.5 |
| 37 | 58 | 18 | 1 | Acetic 1.2 [0.02] | Ac TBA 12.25 [0.05] | 40/100 | 7 | 160 | 1 | 100 | 92.3 | 7.1 | 0.6 |
| 38 | 58 | 54 | 3 | Acetic 0.6 [0.01] | Ac AN 7.65 [0.05] | 20/100 | 6 | 160 | 1 | 100 | 93.7 | 6.0 | 0.3 |
| 39 | 58 | 54 | 3 | Acetic 0.6 [0.01] | Ac PY 6.95 [0.05] | 20/100 | 6 | 160 | 1 | 100 | 94.0 | 5.7 | 0.3 |
| 40 | 58 | 36 | 2 | Acetic 1.2 [0.02] | Ac NH$_4$ 3.08 [0.04] | 50/100 | 6 | 160 | 1 | 100 | 90.8 | 8.2 | 1.0 |
| 41 | 58 | 18 | 1 | Formic 1.38 [0.03] | Ben TMA 5.43 [0.03] | 100/100 | 6 | 140 | 1 | 100 | 94.3 | 5.4 | 0.3 |
| 42 | 58 | 18 | 1 | Formic 0.46 [0.01] | For TMA 4.2 [0.04] | 25/100 | 5 | 140 | 1 | 100 | 94.7 | 5.1 | 0.2 |
| 43 | 58 | 18 | 1 | Propionic 2.96 [0.04] | Pro TMA 3.5 [0.02] | 100/50 | 6 | 160 | 1 | 100 | 92.5 | 7.0 | 0.5 |
| 44 | 58 | 18 | 1 | Cl-Acetic 3.78 [0.04] | ClAcTMA 3.91 [0.02] | 100/50 | 6 | 160 | 1 | 100 | 92.9 | 6.7 | 0.4 |
| 45 | 58 | 18 | 1 | Formic 0.92 [0.02] | Lau TMA 12.95 [0.05] | 40/100 | 7 | 160 | 1 | 100 | 91.0 | 7.9 | 1.1 |
| Compar 11 | 58 | 36 | 2 | — | — | — | — | 160 | 1 | 96.5 | 59.3 | 30.4 | 10.3 |

TABLE 3-continued

| | Material | | | Catalyst | | | | | | | | Product | | |
|---|---|---|---|---|---|---|---|---|---|---|---|---|---|---|
| Example No. | PO (g) | H₂O (g) | H₂O/PO (mole ratio) | (A) Acid (g) [mole] | (B) Salt (g) [mole] | (A)/(B) [mole ratio] | (A) + (B)/PO [% mole] | Reaction Temperature (°C.) | Time (hr) | Conversion (% mole) | PG (% wt) | DPG (% wt) | TPG (% wt) |
| Compar 12 | 58 | 36 | 2 | — | Ac TBA 3.57 [0.03] | 0/100 | 3 | 160 | 1 | 99.5 | 74.7 | 23.2 | 2.1 |
| Compar 13 | 58 | 36 | 2 | Acetic 1.8 [0.03] | — | 100/0 | 3 | 160 | 1 | 100 | 60.2 | 29.4 | 10.4 |
| Compar 14 | 58 | 36 | 2 | — | Ac NH₄ 3.08 [0.04] | 0/100 | 4 | 160 | 1 | 100 | 79.5 | 17.1 | 3.4 |

Note:
PO ... propylene oxide
H₂O ... water
PG ... propylene glycol
DPG ... dipropylene glycol
TPG ... tripropylene glycol
Cl-Acetic ... monochloroacetic acid
Ac TEA ... triethylamine acetate
Ac TBA ... tributylamine acetate
Ac AN ... aniline acetate
Ac PY ... pyridine acetate
Ac NH₄ ... ammonium acetate
Ben TMA ... trimethylamine benzoate
For TMA ... trimethylamine formate
Pro TMA ... trimethylamine propionate
ClAcTMA ... trimethylamine monochloroacetate
Lau TMA ... trimethylamine laurate As stated in detail in the above Examples and Comparative Examples, in the method of this invention for preparing ethylene glycol and/or propylene glycol, the hydration reaction of ethylene oxide and/or propylene oxide is conducted by using the catalyst comprising the carboxylic acid and the carboxylic acid salt or the metal salt of formic acid alone.

Evidently, we can prepare the desired ethylene glycol and/or propylene glycol with a high selectivity and at a high yield even by the hydration reaction which is conducted in an extraordinary high concentration of ethylene oxide and/or propylene oxide as compared with current industrial manufacturing methods such as noncatalytic hydration method or mineral acid catalyzed hydration method.

What is claimed is:

1. A method for preparing ethylene glycol or propylene glycol or both by a hydration reaction of ethylene oxide or propylene oxide or both, which comprises reacting said ethylene oxide or propylene oxide or both with water in the presence of a dual component composition catalyst consisting of (a) a carboxylic acid component and (b) a salt component which is a metal salt of a carboxylic acid or a basic nitrogen-containing compound salt of a carboxylic acid , wherein the mole ratio of said carboxylic acid component (a) to said salt component (b) is 100:1 to 1:100, and
wherein the total quantity of said dual catalyst composition is 0.1 to 50% of ethylene or propylene oxide or both by mole, said carboxylic acid component being a monobasic carboxylic acid having 1 to 20 carbon atoms or a polybasic carboxylic acid having 2 to 20 carbon atoms and said salt component being a salt of such a carboxylic acid.

2. The method as claimed in claim 1 wherein said carboxylic acid salt is a salt of carboxylic acid with an inorganic or organic basic-nitrogen containing compound.

3. The method as claimed in claim 2 wherein the mole ratio of said carboxylic acid to said carboxylic acid salt is 100:3-3:100.

4. The method as claimed in claim 1 wherein said carboxylic acid salt is a metal salt(s) of carboxylic acid.

5. The method as claimed in claim 4 wherein the mole ratio of said carboxylic acid to said metal salt(s) of carboxylic acid is 100:3-3:100.

6. The method as claimed in claim 1, wherein said carboxylic acid, said metal salt and said basic nitrogen-containing salt each have 1-10 carbon atoms.

7. The method as claimed in claim 1, wherein said carboxylic acid, said metal salt and said basic nitrogen-containing salt each have 1-7 carbon atoms.

8. The method as claimed in claim 1, wherein about 1-15 moles of water are used per 1 mole of lower alkylene oxide.

9. The method as claimed in claim 1, wherein said salt component is a metal salt which is an alkali metal salt, an alkaline earth metal salt, a copper group metal salt, zinc group metal salt, aluminum group metal salt, titanium group metal salt, manganese group metal salt or iron group metal salt.

10. The method as in claim 9, wherein said metal salt component is an alkali metal salt or an alkaline earth metal salt.

* * * * *